(12) United States Patent
Borrell

(10) Patent No.: US 11,098,238 B2
(45) Date of Patent: Aug. 24, 2021

(54) TRACER AND METHOD

(71) Applicant: JOHNSON MATTHEY PUBLIC LIMITED COMPANY, London (GB)

(72) Inventor: Neil Borrell, Cleveland (GB)

(73) Assignee: Johnson Mattey Public Limited Company, London (GB)

(*) Notice: Subject to any disclaimer, the term of this patent is extended or adjusted under 35 U.S.C. 154(b) by 327 days.

(21) Appl. No.: 16/072,734

(22) PCT Filed: Jan. 17, 2017

(86) PCT No.: PCT/GB2017/050100
§ 371 (c)(1),
(2) Date: Jul. 25, 2018

(87) PCT Pub. No.: WO2017/129944
PCT Pub. Date: Aug. 3, 2017

(65) Prior Publication Data
US 2019/0062617 A1 Feb. 28, 2019

(30) Foreign Application Priority Data
Jan. 25, 2016 (GB) .................................. 1601320

(51) Int. Cl.
*G01N 33/00* (2006.01)
*C09K 8/58* (2006.01)
(Continued)

(52) U.S. Cl.
CPC ............... *C09K 8/58* (2013.01); *C09K 8/035* (2013.01); *E21B 47/11* (2020.05); *E21B 49/00* (2013.01);
(Continued)

(58) Field of Classification Search
CPC ....................................................... C09K 8/58
(Continued)

(56) References Cited

U.S. PATENT DOCUMENTS 3,856,468 A 12/1974 Keller
4,555,489 A 11/1985 Schmitt
(Continued)

FOREIGN PATENT DOCUMENTS

GB   2526624 A   2/2015
GB   2531318 A   4/2016
WO   WO 2014/096459 A1   6/2014

OTHER PUBLICATIONS

Wei et al., "Estimation of Hydraulic Fracture Volume Utilizing Partitioning Chemical Tracer in Shale Gas Formation," Journal of Natural Gas Science and Engineering, Jul. 2016, 33, 1069-1077.
(Continued)

*Primary Examiner* — Christine T Mui
*Assistant Examiner* — Emily R. Berkeley
(74) *Attorney, Agent, or Firm* — BakerHostetler

(57) ABSTRACT

A method for determining residual oil saturation of an oil reservoir, the method comprising: introducing a partitioning tracer comprising a sulfone compound having a log $K_{ow}$ value in the range −0.5 to 3 into the oil reservoir; and monitoring the production of the tracer from the oil reservoir over time to determine the residual oil saturation. Optionally the method comprises introducing both a conservative tracer and the partitioning tracer into the oil reservoir and monitoring the production of both the tracers from the oil reservoir over time to determine the residual oil saturation.

17 Claims, 2 Drawing Sheets

(51) Int. Cl.
  *C09K 8/035* (2006.01)
  *E21B 49/00* (2006.01)
  *E21B 47/11* (2012.01)
  *G01N 33/28* (2006.01)

(52) U.S. Cl.
  CPC ....... *E21B 49/005* (2013.01); *G01N 33/2823* (2013.01)

(58) Field of Classification Search
  USPC .......................................................... 436/27
  See application file for complete search history.

(56) References Cited

U.S. PATENT DOCUMENTS

| | | |
|---|---|---|
| 4,876,449 A | 10/1989 | Casad et al. |
| 5,168,927 A | 12/1992 | Stegemeier et al. |
| 5,256,572 A | 10/1993 | Tang et al. |

OTHER PUBLICATIONS

"Experimental Aspects of Partitioning Tracer Tests for Residual Oil Saturation Determination With FIA-Based Laboratory Equipment," SPE Reservoir Engineering May 1990, pp. 239-244.
GB1700744.4 Combined Search and Examination Report under Sections 17 and 18(3) dated Jun. 30, 2017.
GB1601320.3 Search Report Under Section 17(5) dated Oct. 4, 2016.
PCT/GB2017/050100 International Search Report and Written Opinion dated Apr. 21, 2017.

TRACER AND METHOD

CROSS-REFERENCE TO RELATED APPLICATIONS

This application is the National Stage of International Patent Application No. PCT/GB2017/050100 filed Jan. 17, 2017, which claims priority from Great Britain Patent Application No. 1601320.3, filed Jan. 25, 2016, the disclosures of each of which are incorporated herein by reference in their entireties for any and all purposes.

FIELD OF THE INVENTION

The present invention relates to use of partitioning tracers for determining a property of a system and methods of determining a property of a system by introducing a conservative and a partitioning tracer into the system and monitoring the production of the tracers from the system over time to determine the property. In particular, but not exclusively, the present invention relates to use of partitioning tracers for determining residual oil saturation in a reservoir and a method of determining residual oil saturation using such tracers.

BACKGROUND

There are several circumstances in which it is desirable to determine the properties of a system using a partitioning tracer. Examples of such systems include oil reservoirs, industrial processes and contaminated aquifers. In order to provide quantitative data it is desirable that the partitioning tracer employed is stable and that any losses of the partitioning tracer are minimised. That includes losses after sampling or during analysis. Losses may occur for example due to evaporation of partitioning tracer, particularly if the sampling or analysis is carried out in hot climates. Many prior art partitioning tracers are suitable for qualitative analysis, where the aim is to confirm whether or not the tracer is present, but not for quantitative analysis where the concentration of partitioning tracer is intended to be linked back to a property of the system being traced.

An example application is the determination of the quantity of oil remaining in an oil formation (the residual oil saturation). For example, the residual oil saturation may be used to determine the most efficient options for recovering oil from the formation later in the life of the formation. It may also be important to assess the residual oil saturation following a water flooding stimulus operation. Methods of determining residual oil saturation are disclosed in U.S. Pat. No. 5,168,927.

A method of determining residual oil saturation, known as the Tang method, is described in U.S. Pat. No. 5,256,572. A non-partitioning (conservative) tracer and a partitioning tracer are injected into the reservoir and their production curves are analysed over time to determine the chromatographic separation of the tracer. The comparison of the production curves involves identifying landmark events such as a peak maximum or a point of maximum rise for each of the tracers and calculating the residual oil saturation (S) directly from the timing or quantity of produced fluids relating to those events.

$$S = \frac{(t_2 - t_1)}{(t_2 + t_1(K-1))} \qquad \text{Equation 1}$$

Where $t_1$ represents the conservative tracer return landmark in either time or quantity of fluid produced, $t_2$ represents the partitioning tracer return landmark in either time or quantity of fluid produced and K represents the partition coefficient (the ratio of the equilibrium concentrations of the tracer in oil and in water) of the partitioning tracer in the reservoir in question. The partition coefficient can be determined for example using the method set out in "Experimental Aspects of Partitioning Tracer Tests for Residual Oil Saturation Determination with FIA-based Laboratory Equipment, SPE Reservoir Engineering, May 1990, pages 239-244".

As the Tang method depends solely on landmarks or events it can be independent of absolute concentration of injected or returned tracer and therefore partial losses of tracer due to decomposition, biological degradation or volatilisation do not affect the prediction of the residual oil saturation.

The compounds typically used as partitioning tracers include alcohols such as ethanol, propanol, and butanol. These compounds suffer from degradation in the reservoir and have relatively poor analytical sensitivity. More recently fluorinated alcohols such as pentafluoropropanol or heptafluorobutanol have been used. These new partitioning tracers may offer better resistance to biological degradation and improved detection limits, however they may be volatile and can suffer significant losses during sampling, transport and storage. The may also suffer losses by partitioning into the gas cap if one exists. WO2014096459 discloses a family of organic tracers for inter-well measurement of residual oil in petroleum reservoirs.

Another method for calculating residual oil saturation based on calculation of temporal moments is gaining popularity. The advantages over the Tang method are that all of the data is used to calculate results and oil volume, swept pore volume and sweep efficiency can also be estimated in addition to the residual oil saturation.

The $k^{th}$ temporal moments of a tracer breakthrough curve ($m_k$) at location x can be defined as $$m_k = \int_{t=0}^{t=\infty} t^k c(x,t) dt \qquad \text{Equation 2}$$

where k is the order of moment, c is the concentration of the tracer and t is time. In order to calculate the residual oil saturation, the mean residence time of the conservative and partitioning tracers are calculated, in each case by dividing the first moment by the zeroth moment. Those mean residence times are then used in equation 1 to determine the residual oil saturation. The method may be advantageous in that it uses all the data, rather than relying on a particular landmark point in the data.

Because the equation above integrates the amount of tracer produced, accurate concentrations of the produced tracer are required in order to produce meaningful results. Whilst it may be possible to make certain corrections to account, for example, for decomposition of tracers, it may not be possible to adequately correct for losses of partitioning tracer due to partitioning into the gas cap, or losses during sampling, storage and transport. The requirement for absolute concentrations renders the existing range of partitioning tracers unsuitable for accurate measurements using the method of moments.

It will be appreciated that the methods of calculating residual oil saturation described above would also be applicable to equivalent circumstances in other fields such as contaminated aquifers or cooling water systems.

Preferred embodiments of the present invention seek to overcome one or more of the above disadvantages of the prior art. In particular, preferred embodiments of the present invention seek to provide improved partitioning tracers for use in determining properties of systems, such as for use in determining residual oil saturation.

SUMMARY OF INVENTION

According to a first aspect of the invention, there is provided use of a partitioning tracer to determine a property of a system wherein the partitioning tracer comprises a sulfone compound having a log $K_{ow}$ value in the range −0.5 to 3. Preferably the log $K_{ow}$ value is in the range 0.5 to 1.5. Those ranges may give optimum partitioning. Preferably the system comprises both aqueous and non-aqueous phases. Preferably the system is an underground formation, such as an oil reservoir or an aquifer. In some embodiments the system may be an industrial process such as a cooling water system in which it is desirable to determine the quantity of a process fluid, such as oil or butanol as examples, with which the coolant water comes into contact.

Preferably the system is an oil reservoir and the property is the residual oil saturation. Thus, preferably the use is of a partitioning tracer for determining residual oil saturation, the partitioning tracer comprising a sulfone compound having a log $K_{ow}$ value in the range −0.5 to 3. Preferably the log $K_{ow}$ value is in the range 0.5 to 1.5. Those ranges may give optimum partitioning into the oil in the formation. If the log $K_{ow}$ value is too high, the partitioning tracer will spend too long in the oil and will not be released from the well in a reasonable time, or even at all. If the log $K_{ow}$ value is too low, the partitioning tracer will largely remain in the water phase and there will not be a sufficient differential between the release of the conservative and partitioning tracers. The log $K_{ow}$ value is the base-10 logarithm of the ratio of the equilibrium concentrations of the tracer in octanol and water and can be determined for example, by the method described in "Experimental Aspects of Partitioning Tracer Tests for Residual Oil Saturation Determination with FIA-based Laboratory Equipment, SPE Reservoir Engineering, May 1990, pages 239-244".

According to a second aspect of the invention, there is provided use of a partitioning tracer to determine a property of a system, the partitioning tracer comprising a sulfone compound according to formula 1:

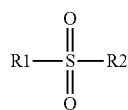

Formula 1

Wherein either:

a. R1 is selected from: methyl, ethyl, propyl, butyl, pentyl, hexyl, ethenyl, propenyl, butenyl, pentenyl, hexenyl or partially or fully halogenated analogues thereof; and R2 is selected from: propyl, butyl, pentyl, hexyl, propenyl, butenyl, pentenyl, hexenyl or partially or fully halogenated analogues thereof or a group according to Formula 2:

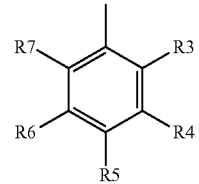

Formula 2

Wherein each of R3, R4, R5, R6 and R7 are individually selected from H, Cl, F, methyl, ethyl, or partially or fully halogenated methyl or ethyl; or b. R1 and R2 are linked, optionally partially or fully halogenated, phenyl groups.

The sulfone compounds of the invention are advantageous in that they are thermally stable, have very low vapour pressures, have good analytical sensitivity and have partition coefficients spanning the range needed for such measurements.

The very low vapour pressure gives the advantages of:
1. Minimal or zero losses when taking hot samples and during transport and storage;
2. Allowing the final eluate to be concentrated by evaporation when solid phase extraction is used to recover the tracer, without causing loss of tracer; and
3. Preventing distortion of results due to the partitioning tracer spending time in a gaseous phase.

The system may be an aquifer in which a level of contamination by non-aqueous phase liquids is to be determined. The system may be a cooling water system in which, typically undesired, interactions of the cooling water with non-aqueous phases are to be determined. The system may comprise aqueous and non-aqueous phases. The aqueous and non-aqueous phases are preferably liquid phases. Preferably one of the phases, preferably the non-aqueous phase, is a stationary phase.

Preferably the system is an oil reservoir and the property is the residual oil saturation. Thus, preferably the use is of a partitioning tracer for determining residual oil saturation. It will be appreciated that the low vapour pressures may be particularly advantageous when using the partitioning tracer to determine residual oil saturation using the method of moments as losses of the tracer between sample collection and analysis may be minimised even in hot climates. However, the advantage of preventing the overestimation of the residual oil saturation in formations with gas caps that can occur due to the partitioning tracer spending time in the gas cap also applies to determining residual oil saturation using the Tang method. Thus the tracers of the invention may be particularly suitable for use when the method of temporal moments is to be used for data analysis and may also offer improved performance when using the landmark method of calculation.

R1 and R2 may be linked phenyl, or fully or partially halogenated phenyl groups. For example $R_1$ and R2 may be linked groups selected from phenyl, chlorophenyl, dichlorophenyl, trichlorophenyl, tetrachlorophenyl, pentachlorophenyl, fluorophenyl, difluorophenyl, trifluorophenyl, tetrafluorophenyl, pentachlorophenyl, bromophenyl, dibromophenyl, tribromophenyl, tetrabromophenyl or pentabromophenyl groups. For example, if $R_1$ and $R_2$ are linked phenyl groups the compound is dibenzothiophene sulfone.

R1 may be selected from $C_nCl_iF_jBr_kH_{2n+1-i-j-k}$ where n is an integer between 1 and 6 and i, j and k are integers independently selected such that $0 \leq i+j+k \leq 2n+1$ or $C_nCl_iF_jBr_kH_{2n-1-i-j-k}$ where n is an integer between 2 and 6 and i, j and k are integers independently selected such that $0 \leq i+j+k \leq 2n-1$. For example, $R_1$ may be selected from $CH_3$, $CH_2Cl$, $CHCl_2$, $CCl_3$, $CH_2F$, $CHF_2$, $CF_3$, $CH_2Br$, $CHBr_2$, $CBr_3$, $C_2H_5$, $C_2H_4Cl$, $C_2H_3Cl_2$, $C_2H_2Cl_3$, $C_2HCl_4$, $C_2Cl_5$, $C_2H_4F$, $C_2H_3F_2$, $C_2H_2F_3$, $C_2HF_4$, $C_2F_5$, $C_2H_4Br$, $C_2H_3Br_2$, $C_2H_2Br_3$, $C_2HBr_4$, $C_2Br_5$, $C_3H_7$, $C_3H_6Cl$, $C_3H_5Cl_2$, $C_3H_4Cl_3$, $C_3H_3Cl_4$, $C_3H_2Cl_5$, $C_3HCl_6$, $C_3Cl_7$, $C_3H_6F$, $C_3H_5F_2$, $C_3H_4F_3$, $C_3H_3F_4$, $C_3H_2F_5$, $C_3HF_6$, $C_3F_7$, $C_3H_6Br$, $C_3H_5Br_2$, $C_3H_4Br_3$, $C_3H_3Br_4$, $C_3H_2Br_5$, $C_3HBr_6$, $C_3Br_7$, $C_4H_9$, $C_4H_8Cl$, $C_4H_7Cl_2$, $C_4H_6Cl_3$, $C_4H_5Cl_4$, $C_4H_4Cl_5$, $C_4H_3Cl_6$, $C_4H_2Cl_7$, $C_4HCl_8$, $C_4Cl_9$, $C_4H_8F$, $C_4H_7F_2$, $C_4H_6F_3$, $C_4H_5F_4$, $C_4H_4F_5$, $C_4H_3F_6$, $C_4H_2F_7$, $C_4HF_8$, $C_4F_9$, $C_4H_8Br$, $C_4H_7Br_2$, $C_4H_6Br_3$, $C_4H_5Br_4$, $C_4H_4Br_5$, $C_4H_3Br_6$, $C_4H_2Br_7$, $C_4HBr_8$, $C_4Br_9$, $C_5H_{11}$, $C_5H_{10}Cl$, $C_5H_9Cl_2$, $C_5H_8Cl_3$, $C_5H_7Cl_4$, $C_5H_6Cl_5$, $C_5H_5Cl_6$, $C_5H_4Cl_7$, $C_5H_3Cl_8$, $C_5H_2Cl_9$, $C_5HCl_{10}$, $C_5Cl_{11}$, $C_5H_{10}F$, $C_5H_9F_2$, $C_5H_8F_3$, $C_5H_7F_4$, $C_5H_6F_5$, $C_5H_5F_6$, $C_5H_4F_7$, $C_5H_3F_8$, $C_5H_2F_9$, $C_5HF_{10}$, $C_5F_{11}$, $C_5H_{10}Br$, $C_5H_9Br_2$, $C_5H_8Br_3$, $C_5H_7Br_4$, $C_5H_6Br_5$, $C_5H_5Br_6$, $C_5H_4Br_7$, $C_5H_3Br_8$, $C_5H_2Br_9$, $C_5HBr_{10}$, $C_5Br_{11}$, $C_6H_{13}$, $C_6H_{12}Cl$, $C_6H_{11}Cl_2$, $C_6H_{10}Cl_3$, $C_6H_9Cl_4$, $C_6H_8Cl_5$, $C_6H_7Cl_6$, $C_6H_6Cl_7$, $C_6H_5Cl_8$, $C_6H_4Cl_9$, $C_6H_3Cl_{10}$, $C_6H_2Cl_{11}$, $C_6HCl_{12}$, $C_6Cl_{13}$, $C_6H_{12}F$, $C_6H_{11}F_2$, $C_6H_{10}F_3$, $C_6H_9F_4$, $C_6H_8F_5$, $C_6H_7F_6$, $C_6H_6F_7$, $C_6H_5F_8$, $C_6H_4F_9$, $C_6H_3F_{10}$, $C_6H_2F_{11}$, $C_6HF_{12}$, $C_6F_{13}$, $C_6H_{12}Br$, $C_6H_{11}Br_2$, $C_6H_{10}Br_3$, $C_6H_9Br_4$, $C_6H_8Br_5$, $C_6H_7Br_6$, $C_6H_6Br_7$, $C_6H_5Br_8$, $C_6H_4Br_9$, $C_6H_3Br_{10}$, $C_6H_2Br_{11}$, $C_6HBr_{12}$, $C_6Br_{13}$, $C_2H_3$, $C_2H_2Cl$, $C_2H_1Cl_2$, $C_2Cl_3$, $C_2H_2F$, $C_2HF_2$, $C_2F_3$, $C_2H_2Br$, $C_2HBr_2$, $C_2Br_3$, $C_3H_5$, $C_3H_4Cl$, $C_3H_3Cl_2$, $C_3H_2Cl_3$, $C_3HCl_4$, $C_3Cl_5$, $C_3H_4F$, $C_3H_3F_2$, $C_3H_2F_3$, $C_3HF_4$, $C_3F_5$, $C_3H_4Br$, $C_3H_3Br_2$, $C_3H_2Br_3$, $C_3HBr_4$, $C_3Br_5$, $C_4H_7$, $C_4H_6Cl$, $C_4H_5Cl_2$, $C_4H_4Cl_3$, $C_4H_3Cl_4$, $C_4H_2Cl_5$, $C_4HCl_6$, $C_4Cl_7$, $C_4H_6F$, $C_4H_5F_2$, $C_4H_4F_3$, $C_4H_3F_4$, $C_4H_2F_5$, $C_4HF_6$, $C_4F_7$, $C_4H_6Br$, $C_4H_5Br_2$, $C_4H_4Br_3$, $C_4H_3Br_4$, $C_4H_2Br_5$, $C_4HBr_6$, $C_4Br_7$, $C_5H_9$, $C_5H_8Cl$, $C_5H_7Cl_2$, $C_5H_6Cl_3$, $C_5H_5Cl_4$, $C_5H_4Cl_5$, $C_5H_3Cl_6$, $C_5H_2Cl_7$, $C_5HCl_8$, $C_5Cl_9$, $C_5H_8F$, $C_5H_7F_2$, $C_5H_6F_3$, $C_5H_5F_4$, $C_5H_4F_5$, $C_5H_3F_6$, $C_5H_2F_7$, $C_5HF_8$, $C_5F_9$, $C_5H_8Br$, $C_5H_7Br_2$, $C_5H_6Br_3$, $C_5H_5Br_4$, $C_5H_4Br_5$, $C_5H_3Br_6$, $C_5H_2Br_7$, $C_5HBr_8$, $C_5Br_9$, $C_6H_{11}$, $C_6H_{10}Cl$, $C_6H_9Cl_2$, $C_6H_8Cl_3$, $C_6H_7Cl_4$, $C_6H_6Cl_5$, $C_6H_5Cl_6$, $C_6H_4Cl_7$, $C_6H_3Cl_8$, $C_6H_2Cl_9$, $C_6HCl_{10}$, $C_6Cl_{11}$, $C_6H_{10}F$, $C_6H_9F_2$, $C_6H_8F_3$, $C_6H_7F_4$, $C_6H_6F_5$, $C_6H_5F_6$, $C_6H_4F_7$, $C_6H_3F_8$, $C_6H_2F_9$, $C_6HF_{10}$, $C_6F_{11}$, $C_6H_{10}Br$, $C_6H_9Br_2$, $C_6H_8Br_2$, $C_6H_7Br_4$, $C_6H_6Br_5$, $C_6H_5Br_6$, $C_6H_4Br_7$, $C_6H_3Br_8$, $C_6H_2Br_9$, $C_6HBr_{10}$, $C_6Br_{11}$. R2 may be selected from $C_mCl_rF_sBr_tH_{2m+1-r-s-t}$ where m is an integer between 3 and 6 and r, s and t are integers independently selected such that $0 \leq r+s+t \leq 2m+1$ or $C_mCl_rF_sBr_tH_{2m-1-r-s-t}$ where m is an integer between 3 and 6 and r, s and t are integers independently selected such that $0 \leq r+s+t \leq 2m-1$ or from Formula 2 wherein each of R3, R4, R5, R6 and R7 are individually selected from $C_pCl_aF_bBr_cH_{2p+1-a-b-c}$ where p is an integer between 0 and 2 and a, b and c are integers independently selected such that $0 \leq a+b+c \leq 2p+1$. Preferably each of R3, R4, R5, R6 and R7 are individually selected from $C_pCl_aF_bH_{2p+1-a-b-c}$ where p is an integer between 0 and 2 and a and b are integers independently selected such that $0 \leq a+b \leq 2p+1$. Thus each of R3, R4, R5, R6 and R7 may be individually selected from H, Cl, F, methyl, ethyl, or partially or fully fluorinated, chlorinated or fluorinated and chlorinated, methyl or ethyl. Preferably each of R3, R4, R5, R6 and R7 are individually selected from H, Cl, F, methyl, ethyl, or partially or fully fluorinated or chlorinated, methyl or ethyl. For example, R2 may be selected from $C_3H_7$, $C_3H_6Cl$, $C_3H_5Cl_2$, $C_3H_4Cl_3$, $C_3H_3Cl_4$, $C_3H_2Cl_5$, $C_3HCl_6$, $C_3Cl_7$, $C_3H_6F$, $C_3H_5F_2$, $C_3H_4F_3$, $C_3H_3F_4$, $C_3H_2F_5$, $C_3HF_6$, $C_3F_7$, $C_3H_6Br$, $C_3H_5Br_2$, $C_3H_4Br_3$, $C_3H_3Br_4$, $C_3H_2Br_5$, $C_3HBr_6$, $C_3Br_7$, $C_4H_9$, $C_4H_8Cl$, $C_4H_7Cl_2$, $C_4H_6Cl_3$, $C_4H_5Cl_4$, $C_4H_4Cl_5$, $C_4H_3Cl_6$, $C_4H_2Cl_7$, $C_4HCl_8$, $C_4Cl_9$, $C_4H_8F$, $C_4H_7F_2$, $C_4H_6F_3$, $C_4H_5F_4$, $C_4H_4F_5$, $C_4H_3F_6$, $C_4H_2F_7$, $C_4HF_8$, $C_4F_9$, $C_4H_8Br$, $C_4H_7Br_2$, $C_4H_6Br_3$, $C_4H_5Br_4$, $C_4H_4Br_5$, $C_4H_3Br_6$, $C_4H_2Br_7$, $C_4HBr_8$, $C_4Br_9$, $C_5H_{11}$, $C_5H_{10}Cl$, $C_5H_9Cl_2$, $C_5H_8Cl_3$, $C_5H_7Cl_4$, $C_5H_6Cl_5$, $C_5H_5Cl_6$, $C_5H_4Cl_7$, $C_5H_3Cl_8$, $C_5H_2Cl_9$, $C_5HCl_{10}$, $C_5Cl_{11}$, $C_5H_{10}F$, $C_5H_9F_2$, $C_5H_8F_3$, $C_5H_7F_4$, $C_5H_6F_5$, $C_5H_5F_6$, $C_5H_4F_7$, $C_5H_3F_8$, $C_5H_2F_9$, $C_5HF_{10}$, $C_5F_{11}$, $C_5H_{10}Br$, $C_5H_9Br_2$, $C_5H_8Br_3$, $C_5H_7Br_4$, $C_5H_6Br_5$, $C_5H_5Br_6$, $C_5H_4Br_7$, $C_5H_3Br_8$, $C_5H_2Br_9$, $C_5HBr_{10}$, $C_5Br_{11}$, $C_6H_{12}Cl$, $C_6H_{12}Cl$, $C_6H_{11}Cl_2$, $C_6H_{10}Cl_3$, $C_6H_9Cl_4$, $C_6H_8Cl_5$, $C_6H_7Cl_6$, $C_6H_6Cl_7$, $C_6H_5Cl_8$, $C_6H_4Cl_9$, $C_6H_3Cl_{10}$, $C_6H_2Cl_{11}$, $C_6HCl_{12}$, $C_6Cl_{13}$, $C_6H_{12}F$, $C_6H_{11}F_2$, $C_6H_{10}F_3$, $C_6H_9F_4$, $C_6H_8F_5$, $C_6H_7F_6$, $C_6H_6F_7$, $C_6H_5F_8$, $C_6H_4F_9$, $C_6H_3F_{10}$, $C_6H_2F_{11}$, $C_6HF_{12}$, $C_6F_{13}$, $C_6H_{12}Br$, $C_6H_{11}Br_2$, $C_6H_{10}Br_3$, $C_6H_9Br_4$, $C_6H_8Br_5$, $C_6H_7Br_6$, $C_6H_6Br_7$, $C_6H_5Br_8$, $C_6H_4Br_9$, $C_6H_3Br_{10}$, $C_6H_2Br_{11}$, $C_6HBr_{12}$, $C_6Br_{13}$, $C_3H_5$, $C_3H_4Cl$, $C_3H_3Cl_2$, $C_3HCl_3$, $C_3HCl_4$, $C_3Cl_5$, $C_3H_4F$, $C_3H_3F_2$, $C_3H_2F_3$, $C_3HF_4$, $C_3F_5$, $C_3H_4Br$, $C_3H_3Br_2$, $C_3H_2Br_3$, $C_3HBr_4$, $C_3Br_5$, $C_4H_7$, $C_4H_6Cl$, $C_4H_5Cl_2$, $C_4H_4Cl_3$, $C_4H_3Cl_4$, $C_4H_2Cl_5$, $C_4HCl_6$, $C_4Cl_7$, $C_4H_6F$, $C_4H_5F_2$, $C_4H_4F_3$, $C_4H_3F_4$, $C_4H_2F_5$, $C_4HF_6$, $C_4F_7$, $C_4H_6Br$, $C_4H_5Br_2$, $C_4H_4Br_3$, $C_4H_3Br_4$, $C_4H_2Br_5$, $C_4HBr_6$, $C_4Br_7$, $C_5H_9$, $C_5H_8Cl$, $C_5H_7Cl_2$, $C_5H_6Cl_3$, $C_5H_5Cl_4$, $C_5H_4Cl_5$, $C_5H_3Cl_6$, $C_5H_2Cl_7$, $C_5HCl_8$, $C_5Cl_9$, $C_5H_8F$, $C_5H_7F_2$, $C_5H_6F_3$, $C_5H_5F_4$, $C_5H_4F_5$, $C_5H_3F_6$, $C_5H_2F_7$, $C_5HF_8$, $C_5F_9$, $C_5H_8Br$, $C_5H_7Br_2$, $C_5H_6Br_3$, $C_5H_5Br_4$, $C_5H_4Br_5$, $C_5H_3Br_6$, $C_5H_2Br_7$, $C_5HBr_8$, $C_5Br_9$, $C_6H_{11}$, $C_6H_{10}Cl$, $C_6H_9Cl_2$, $C_6H_8Cl_3$, $C_6H_7Cl_4$, $C_6H_6Cl_5$, $C_6H_5Cl_6$, $C_6H_4Cl_7$, $C_6H_3Cl_5$, $C_6H_2Cl_9$, $C_6HCl_{10}$, $C_6Cl_{11}$, $C_6H_{10}F$, $C_6H_9F_2$, $C_6H_8F_3$, $C_6H_7F_4$, $C_6H_6F_5$, $C_6H_5F_6$, $C_6H_4F_7$, $C_6H_3F_8$, $C_6H_2F_9$, $C_6HF_{10}$, $C_6F_{11}$, $C_6H_{10}Br$, $C_6H_9Br_2$, $C_6H_8Br_2$, $C_6H_7Br_4$, $C_6H_6Br_5$, $C_6H_5Br_6$, $C_6H_4Br_7$, $C_6H_3Br_8$, $C_6H_2Br_9$, $C_6HBr_{10}$, $C_6Br_{11}$ or from Formula 2 wherein each of R3, R4, R5, R6 and R7 are individually selected from H, Cl, F, $CH_3$, $CH_2Cl$, $CHCl_2$, $CCl_3$, $CH_2F$, $CHF_2$, $CF_3$, $C_2H_5$, $C_2H_4Cl$, $C_2H_3Cl_2$, $C_2H_2Cl_3$, $C_2HCl_4$, $C_2Cl_5$, $C_2H_4F$, $C_2H_3F_2$, $C_2H_2F_3$, $C_2HF_4$, $C_2F_5$.

Preferably R1 is selected from: methyl, ethyl, propyl, butyl, pentyl, hexyl, ethenyl, propenyl, butenyl, pentenyl, hexenyl or partially or fully halogenated analogues thereof; and R2 is a group according to Formula 2:

Formula 2

Wherein each of R3, R4, R5, R6 and R7 are individually selected from H, Cl, F, methyl, ethyl, or partially or fully halogenated methyl or ethyl. Thus R1 is an, optionally halogenated, alkyl and R2 is an, optionally halogenated, phenyl, methylphenyl or ethylphenyl. Such compounds may have particularly favourable partitioning coefficients and therefore show sufficient preference for oil to exhibit a significant delay relative to the conservative tracer, but not so much preference that they take too long to be produced.

Preferable compounds, with their log $K_{ow}$ values indicated, include:

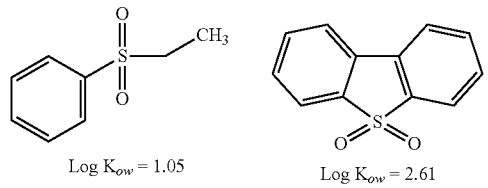

Log $K_{ow}$ = 1.05    Log $K_{ow}$ = 2.61

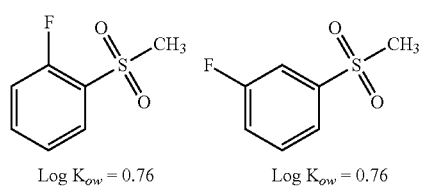

Log $K_{ow}$ = 0.76    Log $K_{ow}$ = 0.76

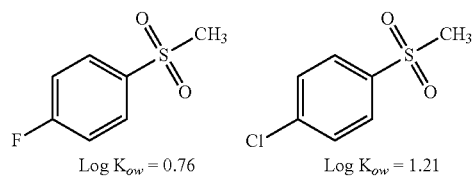

Log $K_{ow}$ = 0.76    Log $K_{ow}$ = 1.21

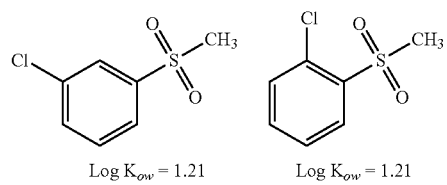

Log $K_{ow}$ = 1.21    Log $K_{ow}$ = 1.21

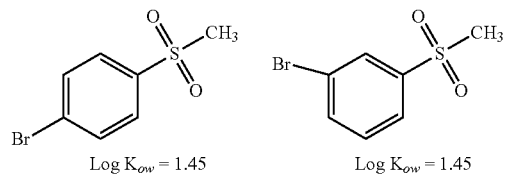

Log $K_{ow}$ = 1.45    Log $K_{ow}$ = 1.45

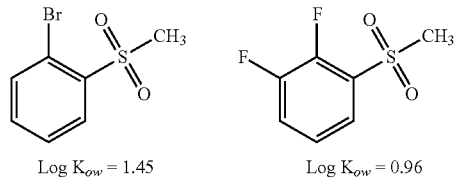

Log $K_{ow}$ = 1.45    Log $K_{ow}$ = 0.96

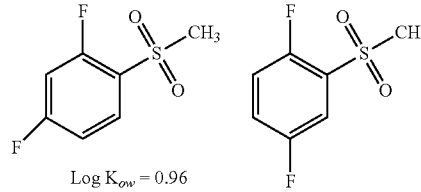

Log $K_{ow}$ = 0.96    Log $K_{ow}$ = 0.96

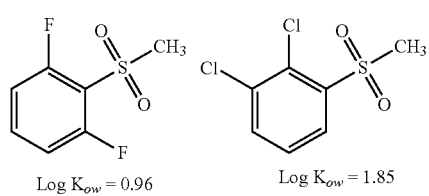

Log $K_{ow}$ = 0.96    Log $K_{ow}$ = 1.85

-continued

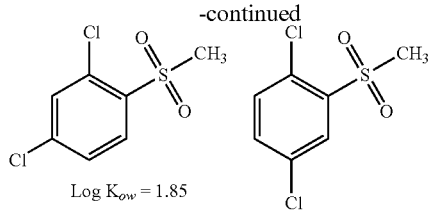

Log $K_{ow}$ = 1.85    Log $K_{ow}$ = 1.85

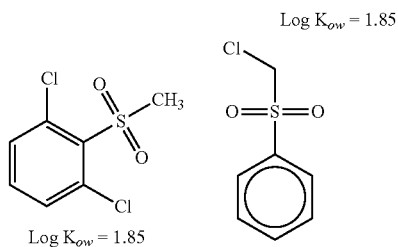

Log $K_{ow}$ = 1.85    Log $K_{ow}$ = 1.24

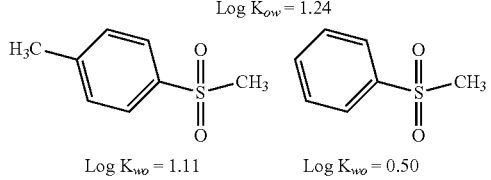

Log $K_{wo}$ = 1.11    Log $K_{wo}$ = 0.50

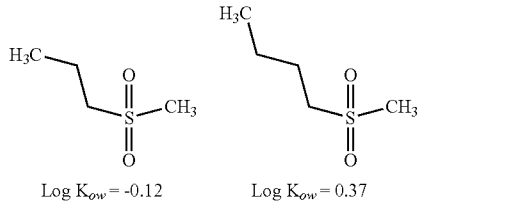

Log $K_{ow}$ = -0.12    Log $K_{ow}$ = 0.37

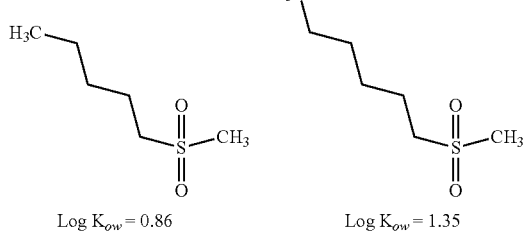

Log $K_{ow}$ = 0.86    Log $K_{ow}$ = 1.35

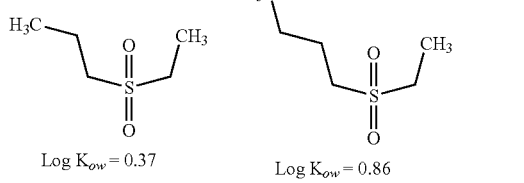

Log $K_{ow}$ = 0.37    Log $K_{ow}$ = 0.86

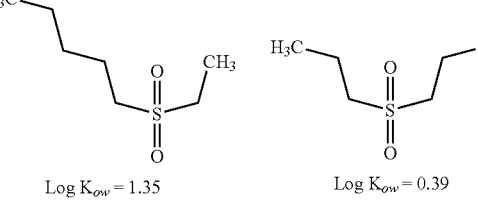

Log $K_{ow}$ = 1.35    Log $K_{ow}$ = 0.39

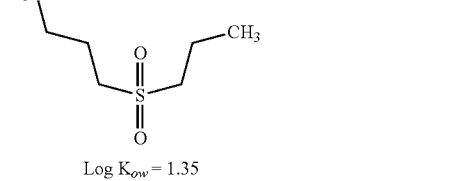

Log $K_{ow}$ = 1.35

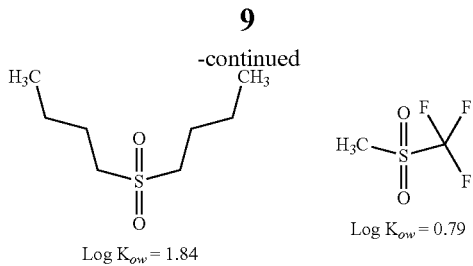
The log $K_{ow}$ values are either experimentally determined or estimated using KOWWIN v1.68.
More preferred compounds include:
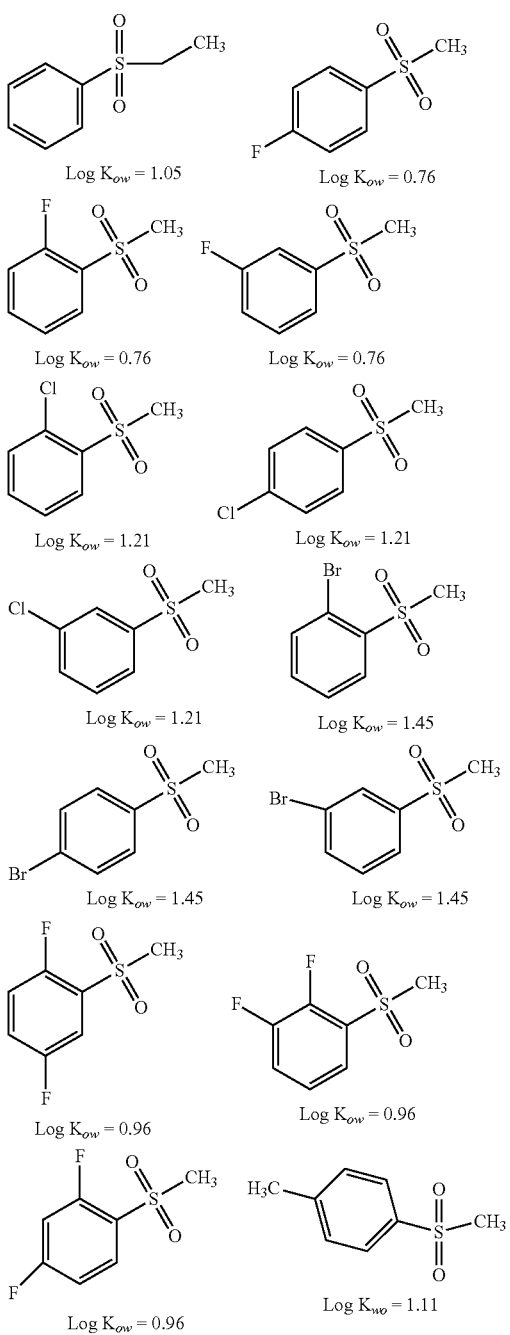
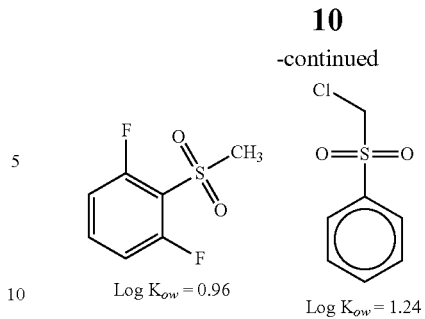
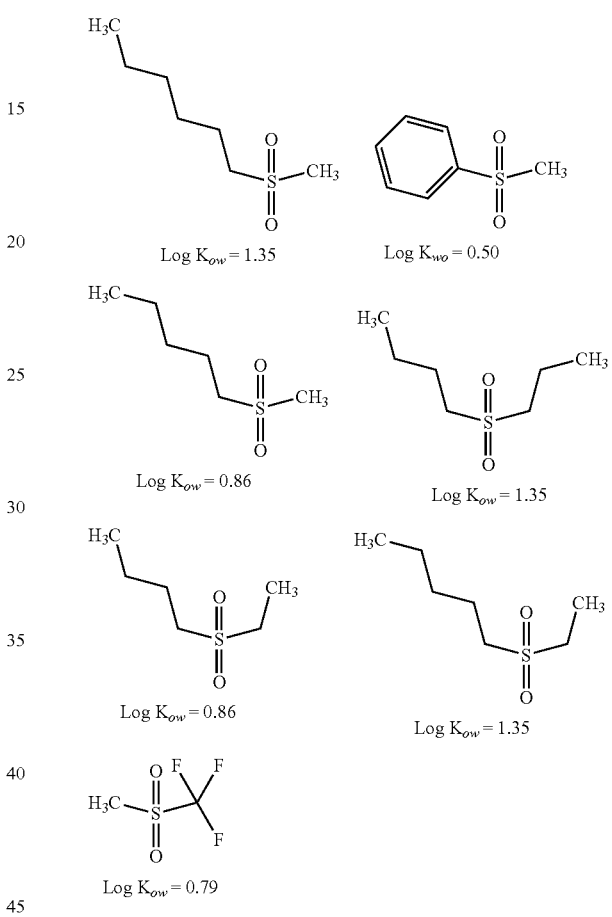
Those compounds have particularly favourable log $K_{ow}$ values.
Most preferred compounds include:
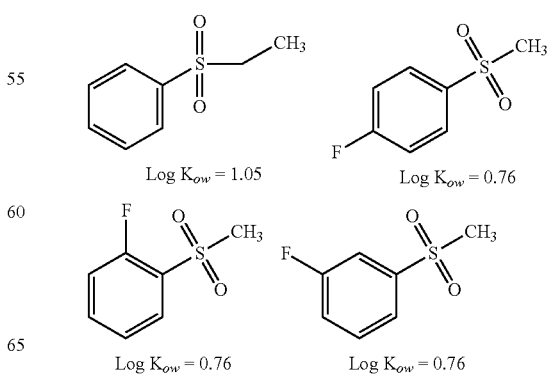

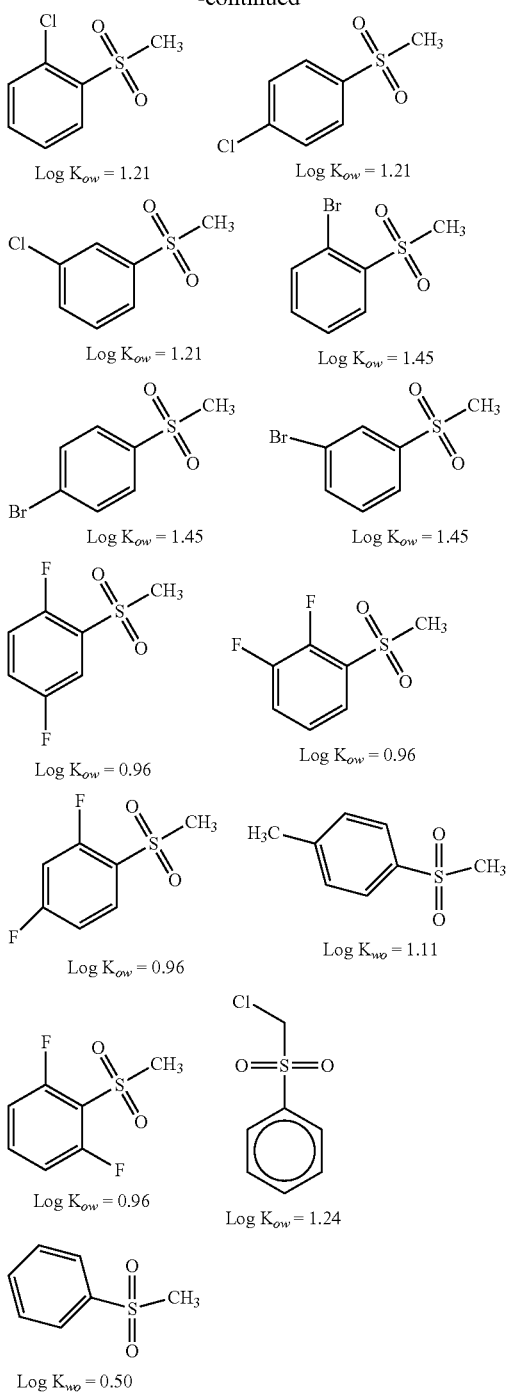

Those compounds have been found to have favourable log $K_{ow}$, stability, vapour pressure and detectability characteristics.

Preferably the sulfone compound has a log $K_{ow}$ of from −0.5 to 3, more preferably from 0.5 to 3 and most preferably from 0.5 to 1.5. Such a log $K_{ow}$ may indicate that the sulfone will act as a partitioning tracer, giving enough distinguishability in residence time from the conservative tracer, without unnecessarily prolonging the test. If the log $K_{ow}$ is too low, then the partitioning tracer will not act as a partitioning tracer. For example, dimethylsulfone has a log $K_{ow}$ value of −1.11 and thus would not be suitable as a partitioning tracer. Thus it may be that the partitioning tracer is not dimethylsulfone.

According to a third aspect of the invention there is provided a method of determining a property of a system, the method comprising introducing a conservative tracer and a partitioning tracer into the system and monitoring the production of the tracers from the system over time to determine the property, wherein the partitioning tracer comprises a sulfone compound having a log $K_{ow}$ value in the range −0.5 to 3. Preferably the log $K_{ow}$ value is in the range 0.5 to 1.5. Preferably the tracers are injected into the system. Preferably the system comprises an aqueous and a non-aqueous phase. Preferably the non-aqueous phase is a stationary phase. Preferably the method is a method of determining the residual oil saturation in a reservoir, the method comprising introducing, for example injecting, a conservative tracer and a partitioning tracer into the reservoir and monitoring for the tracers, for example for the production of the tracers from the reservoir, over time to determine the residual oil saturation wherein the partitioning tracer comprises a sulfone compound having a log $K_{ow}$ value in the range −0.5 to 3. Preferably the log $K_{ow}$ value is in the range 0.5 to 1.5.

According to a fourth aspect of the invention, there is provided a method of determining a property of a system, the method comprising introducing a conservative tracer and a partitioning tracer into the system and monitoring for the tracers over time to determine the property of the system, wherein the partitioning tracer comprises a sulfone compound according to formula 1:

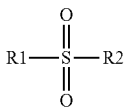

Formula 1

Wherein either:
a. R1 is selected from: methyl, ethyl, propyl, butyl, pentyl, hexyl, ethenyl, propenyl, butenyl, pentenyl, hexenyl or partially or fully halogenated analogues thereof; and R2 is selected from: propyl, butyl, pentyl, hexyl, propenyl, butenyl, pentenyl, hexenyl or partially or fully halogenated analogues thereof or a group according to Formula 2:

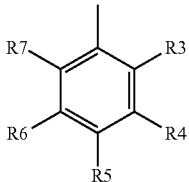

Formula 2

Wherein each of R3, R4, R5, R6 and R7 are individually selected from H, Cl, F, methyl, ethyl, or partially or fully halogenated methyl or ethyl; or
b. R1 and R2 are linked, optionally partially or fully halogenated, phenyl groups.

Preferably the tracers are injected into the system. Preferably the system comprises an aqueous and a non-aqueous phase. Preferably the non-aqueous phase is a stationary phase.

The system may be an aquifer in which a level of contamination by non-aqueous phase liquids is to be determined. The system may be a cooling water system in which, typically undesired, interactions of the cooling water with non-aqueous phases are to be determined.

Preferably the method is a method of determining the residual oil saturation in a reservoir, the method comprising introducing a conservative tracer and a partitioning tracer into the reservoir and monitoring for the tracers over time to determine the residual oil saturation, wherein the partitioning tracer comprises the sulfone compound. Preferably the tracers are introduced by injection into the well. Preferably the monitoring comprises monitoring the production of the tracers from the reservoir.

Further aspects of the partitioning tracer may be as set out above in relation to the first and second aspects of the invention.

Preferably the method includes the step of using the method of moments to determine the property of the system. For example the method may include the step of using the method of moments to calculate the residual oil saturation in the reservoir. Thus the method may include the steps of: taking a series of samples of the fluid produced from the system (e.g. the reservoir) at different times; analysing the samples to determine the concentration of the tracers in each sample; calculating a mean residence time for each tracer by dividing the first moment of the breakthrough curve by the zeroth moment of the breakthrough curve and calculating the property (e.g. the residual oil saturation) from the mean residence times.

The zeroth and first moments at location x may be calculated by using k=0 and k=1, respectively, in the formula:

$$m_k = \int_{t=0}^{t=\infty} t^k c(x,t) dt \qquad \text{Equation 2}$$

where $m_k$ is the $k^{th}$ order moment, k is the order of moment, c is the concentration of the tracer and t is time.

The property (e.g. the residual oil saturation) may be calculated by $$s = \frac{(t_2 - t_1)}{(t_2 + t_1(K-1))} \qquad \text{Equation 1}$$

Where $t_1$ and $t_2$ are the mean residence times of the conservative and partitioning tracers respectively and K is the partition coefficient of the partitioning tracer.

The analysis of the samples may take place at the location of the system or at a remote laboratory. For example the remote laboratory may be several, for example at least 10 or at least 100, miles from the system, or in a different country, or even on a different continent. The samples may be analysed some time, for example a week or more, after the samples are obtained from fluid flowing from the system. It will be appreciated that the low vapour pressure and high stability of the partitioning tracers of the present invention reduce losses during storage and transport and therefore allow the analysis to be performed at a time and location different to those at which the sample is obtained.

The method may include injecting more than one partitioning tracer into the system, for example each partitioning tracer may be injected at a different location, each of the partitioning tracers being a sulfone compound as described above. The partitioning tracers of the invention may be particularly advantageous in such methods as they are distinguishable from each other during the analysis.

The conservative tracer may for example be a known tracer with low partitioning coefficient. Typical conservative tracers used in methods of determining residual oil saturation, and suitable for use in the methods of the present invention, include fluorobenzoic acid salts, naphthalene sulfonic acid salts, sodium thiocyanate and sodium bromide.

It will be appreciated that features described in relation to one aspect of the invention may be equally applicable in another aspect of the invention. For example, features described in relation to the use of the invention, may be equally applicable to the method of the invention, and vice versa. Some features may not be applicable to, and may be excluded from, particular aspects of the invention.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
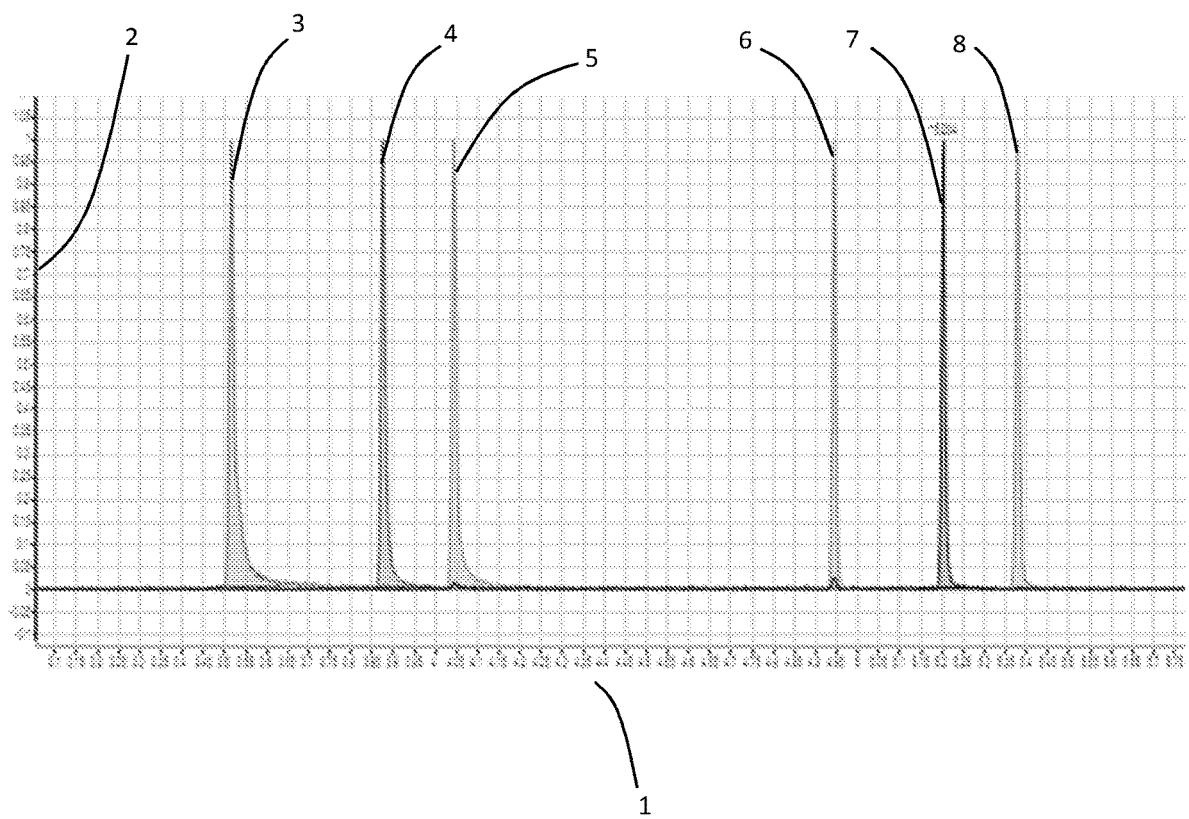
FIG. 1 is a representative GC-MS chromatogram of six partitioning tracers according to the invention.

In FIG. 1 a GC-MS chromatogram plots counts 2 against retention time 1. Data are plotted for 6 example sulfone partitioning tracers 3, 4, 5, 6, 7, and 8 having log $K_{ow}$ values spread across the range from −0.5 to 3. The tracers 3, 4, 5, 6, 7, and 8 have been passed through the GC after solid phase extraction from a sample of produced water from a formation that has previously produced hydrocarbon and now produces a significant quantity of produced water (a so-called "watered out field"). Each of the tracers 3, 4, 5, 6, 7, and 8 produces a clear signal at a different retention time. Thus the tracers 3, 4, 5, 6, 7, and 8 are distinguishable both from compounds in produced water and each other.

Figure 2:
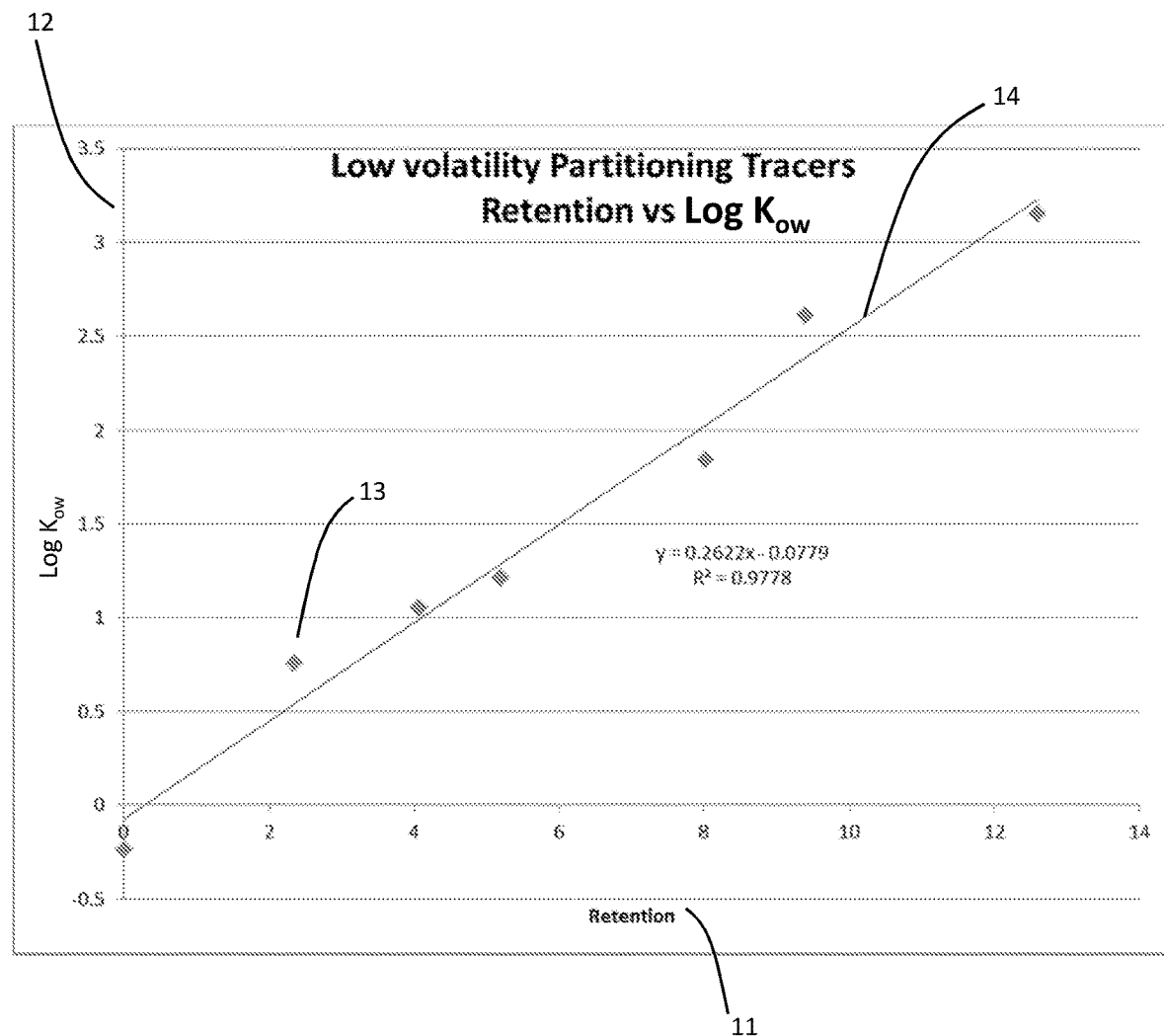
FIG. 2 is a graph plot of retention of partitioning tracers according to the invention on an oil saturated column against measured log $K_{ow}$ value for those partitioning tracers.

In FIG. 2, log $K_{ow}$ 12 is plotted against retention 11 in an oil saturated column. The data 13 fits a straight line correlation 14, suggesting that the sulfone partitioning tracers all behave similarly in terms of their interaction with the oil being determined by their partitioning coefficient and are therefore suitable for use in determining residual oil saturation using the landmark (Tang) method or the method of temporal moments.

The following table contains partition coefficient and vapour pressure data for a partitioning tracer according to the invention (4-chlorophenyl methyl sulfone) and two prior art partitioning tracers (1,1,1,3,3,3-hexafluoro-2-propanol and 4-chlorobenzyl alcohol). It can be seen that the log $K_{ow}$ of the partitioning tracer according to the invention falls within the most desirable range and that the vapour pressure of the partitioning tracer according to the invention is significantly lower than either of the two prior art partitioning tracers. Thus the partitioning tracer according to the invention is less susceptible to losses due to vaporisation during sampling, storage and transport and is less likely to spend time in any gas cap within the formation. As a result more accurate calculations of the residual oil saturations may be performed.

| Compound | Log $K_{ow}$ | Vapour Pressure |
| --- | --- | --- |
| 4-Chlorophenyl methyl sulfone | 1.21 | 0.000987 mm Hg |
| 1,1,1,3,3,3-Hexafluoro-2-propanol | 1.66 | 156 mm Hg |
| 4-Chlorobenzyl alcohol | 1.72 | 0.00268 mm Hg |

It will be appreciated by persons skilled in the art that the above embodiments have been described by way of example only, and not in any limitative sense, and that various alterations and modifications are possible without departure from the scope of the invention as defined by the appended claims.

The invention claimed is:

1. A method for determining residual oil saturation of an oil reservoir, the method comprising: introducing a partitioning tracer comprising a sulfone compound having a log $K_{ow}$ value in the range −0.5 to 3 into the oil reservoir; and monitoring the production of the tracer from the oil reservoir over time to determine the residual oil saturation.

2. The method according to claim 1, the method comprising introducing both a conservative tracer and the partitioning tracer into the oil reservoir and monitoring the production of both the tracers from the oil reservoir over time to determine the residual oil saturation.

3. The method according to claim 2, wherein the log $K_{ow}$ value is in the range 0.5 to 1.5.

4. The method according to claim 1, wherein the sulfone compound is according to formula 1:

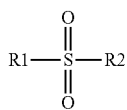

Formula 1 wherein either:
- a. R1 is selected from: methyl, ethyl, propyl, butyl, pentyl, hexyl, ethenyl, propenyl, butenyl, pentenyl, hexenyl or partially or fully halogenated analogues thereof; and R2 is selected from: propyl, butyl, pentyl, hexyl, propenyl, butenyl, pentenyl, hexenyl or partially or fully halogenated analogues thereof or a group according to Formula 2:

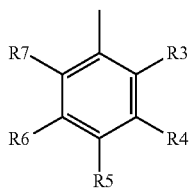

Formula 2 wherein each of R3, R4, R5, R6 and R7 are individually selected from H, Cl, F, methyl, ethyl, or partially or fully halogenated methyl or ethyl; or
- b. R1 and R2 are linked, optionally partially or fully halogenated, phenyl groups.

5. The method according to claim 2, wherein the sulfone compound is according to formula 1:

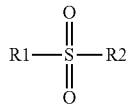

Formula 1 wherein either:
- a. R1 is selected from: methyl, ethyl, propyl, butyl, pentyl, hexyl, ethenyl, propenyl, butenyl, pentenyl, hexenyl or partially or fully halogenated analogues thereof; and R2 is selected from: propyl, butyl, pentyl, hexyl, propenyl, butenyl, pentenyl, hexenyl or partially or fully halogenated analogues thereof or a group according to Formula 2:

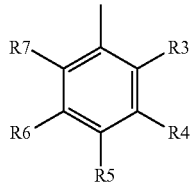

Formula 2 wherein each of R3, R4, R5, R6 and R7 are individually selected from H, Cl, F, methyl, ethyl, or partially or fully halogenated methyl or ethyl; or
- b. R1 and R2 are linked, optionally partially or fully halogenated, phenyl groups.

6. The method of claim 4, wherein R1 and R2 are linked phenyl groups, or linked fully or partially halogenated phenyl groups.

7. The method of claim 6, wherein R1 and R2 are linked groups independently selected from phenyl, chlorophenyl, dichlorophenyl, trichlorophenyl, tetrachlorophenyl, pentachlorophenyl, fluorophenyl, difluorophenyl, trifluorophenyl, tetrafluorophenyl, pentafluorophenyl, bromophenyl, dibromophenyl, tribromophenyl, tetrabromophenyl or pentabromophenyl groups.

8. The method of claim 4, wherein R1 is selected from: methyl, ethyl, propyl, butyl, pentyl, hexyl, ethenyl, propenyl, butenyl, pentenyl, hexenyl or partially or fully halogenated analogues thereof; and R2 is a group according to Formula 2:

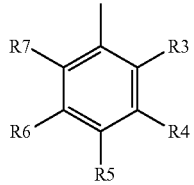

Formula 2

Wherein each of R3, R4, R5, R6 and R7 are individually selected from H, Cl, F, methyl, ethyl, or partially or fully halogenated methyl or ethyl.

9. The method of claim 4, wherein the sulfone compound has a partitioning coefficient of from 0.5 to 3.

10. The method according to claim 9, wherein the sulfone compound has a partitioning coefficient of from 0.5 to 1.5.

11. The method of claim 2, wherein the residual oil saturation is determined using the method of temporal moments.

12. The method of claim 1, wherein the residual oil saturation is determined using the Tang method.

13. The method of claim 1, wherein the residual oil saturation is determined by analysing samples comprising the partitioning tracer at a remote laboratory.

14. The method of claim 1, wherein the oil reservoir comprises an aqueous and a non-aqueous phase.

15. The method of claim 5, wherein R1 is selected from: methyl, ethyl, propyl, butyl, pentyl, hexyl, ethenyl, propenyl, butenyl, pentenyl, hexenyl, or partially or fully halogenated analogues thereof; and R2 is a group according to Formula 2:

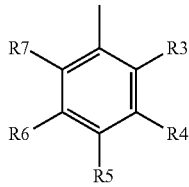

Formula 2 wherein each of R3, R4, R5, R6 and R7 are individually selected from H, Cl, F, methyl, ethyl, or partially or fully halogenated methyl or ethyl.

16. The method of claim 1, wherein the log $K_{ow}$ value is in the range 0.5 to 1.5.

17. The method of claim 5, wherein R1 and R2 are linked phenyl groups, or linked fully or partially halogenated phenyl groups.

* * * * *